United States Patent
Eslami et al.

(10) Patent No.: US 10,264,961 B2
(45) Date of Patent: Apr. 23, 2019

(54) METHOD FOR VISUALIZING A MEMBRANE ON A RETINA OF AN EYE AND SURGICAL MICROSCOPE FOR PERFORMING THE METHOD

(71) Applicant: Carl Zeiss Meditec AG, Jena (DE)

(72) Inventors: Abouzar Eslami, Munich (DE); Corinna Maier-Matic, Neuried (DE); Falk Hartwig, Munich (DE); Christine Kochwagner, Rott am Inn (DE); Stefan Duca, Poing (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/253,468

(22) Filed: Aug. 31, 2016

(65) Prior Publication Data

US 2017/0055821 A1 Mar. 2, 2017

(30) Foreign Application Priority Data

Sep. 1, 2015 (DE) .......... 10 2015 011 420

(51) Int. Cl.
*A61B 3/14* (2006.01)
*A61B 3/00* (2006.01)
(Continued)

(52) U.S. Cl.
CPC .......... *A61B 3/0025* (2013.01); *A61B 3/0041* (2013.01); *A61B 3/12* (2013.01); *A61B 3/13* (2013.01); *A61B 3/14* (2013.01)

(58) Field of Classification Search
CPC ......... A61B 3/102; A61B 3/12; A61B 3/1241; A61B 3/13; A61B 3/14
(Continued)

(56) References Cited

U.S. PATENT DOCUMENTS 6,372,449 B1 4/2002 Coroneo
6,840,933 B1 * 1/2005 Pang .................... A61B 3/1241
600/479

(Continued)

FOREIGN PATENT DOCUMENTS

EP 2 620 144 A1 7/2013
WO 2012/156372 A1 11/2012

OTHER PUBLICATIONS

English translation and the Office action of the German Patent Office dated Jun. 14, 2016 in German patent application 10 2015 011 420.4 on which the claim of priority is based.

*Primary Examiner* — Mahidere S Sahle
(74) *Attorney, Agent, or Firm* — Walter Ottesen, P.A.

(57) ABSTRACT

A method for visualizing a membrane on a retina of an eye includes recording a first image of the retina of the eye, wherein the membrane on the retina of the eye is not stained, recording a second image of the retina of the eye after the membrane on the retina of the eye has been stained, determining a first transformation such that mutually corresponding structures of the retina of the eye are located at mutually corresponding places in the second image and in the first image which was transformed with the first transformation, identifying image regions in the second image, which contain the membrane on the retina, based on the transformed first image and the recorded second image, and displaying the second image such that the identified image regions in the second image are highlighted relative to the surroundings of the identified image regions.

16 Claims, 3 Drawing Sheets

(51) Int. Cl.
*A61B 3/12* (2006.01)
*A61B 3/13* (2006.01)

(58) Field of Classification Search
USPC .......................................................... 351/206
See application file for complete search history.

(56) References Cited

U.S. PATENT DOCUMENTS

| | | |
|---|---|---|
| 7,070,619 B2 | 7/2006 | Snyder et al. |
| 2006/0235068 A1 | 10/2006 | Snyder et al. |
| 2010/0103250 A1 | 4/2010 | Ishihara |
| 2013/0301001 A1* | 11/2013 | Carnevale ............... G06T 11/60 351/206 |
| 2013/0307960 A1 | 11/2013 | Bahm et al. |
| 2014/0160264 A1 | 6/2014 | Taylor et al. |
| 2014/0362343 A1* | 12/2014 | Hauger .................... A61B 3/13 351/206 |

* cited by examiner

METHOD FOR VISUALIZING A MEMBRANE ON A RETINA OF AN EYE AND SURGICAL MICROSCOPE FOR PERFORMING THE METHOD

CROSS REFERENCE TO RELATED APPLICATION

This application claims priority of German patent application no. 10 2015 011 420.4, filed Sep. 1, 2015, the entire content of which is incorporated herein by reference.

FIELD OF THE INVENTION

The present invention relates to a method for visualizing a membrane on a retina of an eye and to a surgical microscope for performing the method.

BACKGROUND OF THE INVENTION

Epiretinal gliosis is a disease of the eyes, in which the posterior vitreous changes, with a see-through, cellophane-type membrane forming on the central retina. This membrane is transparent or semitransparent and typically has a thickness of a few micrometers. The membrane gradually shrinks and as a result deforms the retina. This causes the retina to pucker, which can result in the central visual acuity of the patient being reduced and visual perception being distorted. The mechanical forces which are exerted on the tissue of the retina result in an accumulation of water, which causes the retina to swell. This additionally reduces the central visual acuity. If the patient's vision becomes too limited, the epiretinal gliosis must be treated by way of an intervention.

During this intervention, first the posterior vitreous is removed. Next, the epiretinal membrane is peeled off the retina using tweezers, with the membrane being plucked from the retina at a flat angle using the tweezers. If necessary, the surgeon additionally removes the internal limiting membrane, via which a significantly lower recurrence rate can be achieved. Removal of the epiretinal membrane or the internal limiting membrane is referred to in each case as membrane peeling.

Membrane peeling makes high demands on the surgeon. The membrane is difficult to see using traditional microscopes. For this reason, membrane peeling is sometimes referred to as the most difficult intervention that is carried out on the eye.

In order to differentiate the membrane from underlying and surrounding healthy tissue, a dye is generally used in conventional interventions that selectively stains the tissue structures of the epiretinal membrane or of the internal limiting membrane. However, several of these dyes have been subject to critical discussions in respect of potential toxicity. The dye must typically be used with the highest possible degree of dilution in order to exclude any toxic effect as much as possible, which in turn results in a lower color contrast of the stained membranes and thus poorer visibility of the membranes for the surgeon.

SUMMARY OF THE INVENTION

It is an object of the invention to propose a method for visualizing a membrane on a retina of an eye, which provides better visibility of the membrane for a surgeon. It is furthermore an object of the present invention to propose a surgical microscope, with which such a method can be performed.

According to a first embodiment, a method for visualizing a membrane of a retina of an eye includes: recording a first image of the retina of the eye, wherein the membrane on the retina of the eye is not stained; recording a second image of the retina of the eye after the membrane on the retina of the eye has been stained; determining a first transformation such that mutually corresponding structures of the retina of the eye are located at mutually corresponding places in the second image and in the first image which was transformed with the first transformation; identifying image regions in the second image, which substantially completely contain the membrane on the retina and substantially exclusively contain the membrane of the retina, specifically based on the transformed first image and the recorded second image; presenting the second image such that the identified image regions in the second image are highlighted relative to the surrounding area of the identified image regions.

According to one embodiment, a surgical microscope includes a microscope optics, a camera, a display apparatus, and a controller which is configured to perform the above-mentioned method by controlling the components of the microscope and by image processing.

The first image can be recorded with the camera of the microscope. Recording of the first image can be triggered by way of a command by a user of the microscope. This command can be issued by the user for example by way of operating a switch which is connected to the controller or by way of a voice command, which is detected via a microphone that is connected to the controller and is recognized by a speech analysis module of the controller.

The first image is recorded at a time at which the dye for staining the membrane has not yet been applied. This dye is applied after the first image is recorded in order to stain the membrane on the retina of the eye. Next, the second image of the retina of the eye is recorded. Recording of the second image can be triggered in a similar way to the previously described recording of the first image.

Between the recording of the first image and recording of the second image, the eye has typically displaced relative to the camera, or the surgeon has changed a setting of the microscope, such as for example magnification of the microscope, between the recording of the first and the second images. As a result, mutually corresponding structures of the retina of the eye in the first image and the second image are not located at mutually corresponding places, which is why it is difficult for automated image processing to identify the stained membrane of the retina correctly by comparing the first image to the second image. For this reason, the first transformation is determined, which is such that mutually corresponding structures of the retina of the eye are located at mutually corresponding places in the second image and in the first image that has been transformed with the first transformation. The first transformation can be characterized, for example, by parameters which describe a translation, a rotation and/or scaling of the first image.

After application of the first transformation to the first image, the transformed first image and the second image can be analyzed by automated image processing to identify in the second image image regions which correspond to the stained membrane on the retina. In the process, the image regions are identified such that the identified image regions contain the membrane on the retina substantially completely and exclusively.

Identifying the image regions in the second image can include an image processing step of background removal. Here, the background corresponds to those structures of the retina which are not overlaid by the membrane, and the foreground corresponds to those regions of the second image which contain the stained membrane. It is assumed here that the regions of the retina which are not overlaid by the membrane are contained in the first image and the second image unchanged and are located at substantially identical sites in the first image and in the second image due to the application of the first transformation. The regions of the retina which are not overlaid by the membrane are thus statically contained in the first and the second image. On the other hand, the regions of the first and the second image that contain the membrane have dynamically changed between the recording of the first and the second image due to the staining of the membrane. In the course of the image processing step of background removal, static image regions are considered as background and dynamically changing image regions as foreground. The background that is identified in this way can be removed from the second image, with the result that only those regions that represent the membrane remain in the second image.

Furthermore, an image processing step of digital subtraction between the first and the second image can be carried out. In the case of such a subtraction, structures which are statically contained in the first and the second image and thus the regions of the retina that are not overlaid by the membrane will substantially not be contained in the difference image, whereas dynamically changed structures and thus those image regions that contain the membrane will remain in the difference image. Before subtraction, the first and/or the second image can be processed so as to match, for example, brightnesses and/or contrasts in the two images to one another, with the result that the static regions are better suppressed. The image processing steps of background removal and digital subtraction can also be carried out together.

After the image regions of the second image that correspond to the membrane have been identified, the second image is presented such that the identified image regions in the second image are highlighted relative to the surrounding area of the identified image regions. Presenting can be effected using the display apparatus of the surgical microscope. Highlighting can be effected in that the identified image regions are superimposed on the second image with increased brightness and/or in a specific color, with the result that the identified image regions in the presented image visibly stand out from the remaining regions of the second image owing to increased brightness and/or a specific color.

This enables the user of the microscope to differentiate the membrane on the retina of the eye from the area surrounding it and to plan the intervention with respect to the removal of the membrane.

The steps of recording the second image, determining the first transformation, identifying the image regions, and presenting the second image with the highlighted identified image regions can be carried out repeatedly. The repetition rate can here be limited by the processing speed of the image processing for identifying the image regions in the second image. With a sufficiently high repetition rate, the user can observe the repeated presentations of the second image with highlighted identified image regions in the form of a live image in real time and on the basis thereof perform his manipulations with surgical tools on the membrane.

According to a second embodiment, a method for visualizing a membrane of a retina of an eye includes: recording a first image of the retina of the eye, wherein the membrane on the retina of the eye is not stained; recording a second image of the retina of the eye after the membrane on the retina of the eye has been stained; determining a first transformation such that mutually corresponding structures of the retina of the eye are located at mutually corresponding places in the second image and in the first image which was transformed with the first transformation; identifying image regions in the second image, which substantially completely contain the membrane on the retina and substantially exclusively contain the membrane of the retina, specifically based on the transformed first image and the recorded second image; recording a third image of the retina of the eye after the second image has been recorded, determining a second transformation such that mutually corresponding structures of the retina of the eye are located at mutually corresponding places in the third image and in the second image that has been transformed with the second transformation, and presenting the third image in superposition with the identified image regions which have been transformed with the second transformation.

This method can be performed with a surgical microscope in similar fashion to the method of the previously explained first embodiment. Method steps which have already been explained will not be explained again for the present embodiment so as to avoid repetition.

The method of the second embodiment is advantageous over the method of the first embodiment if the image processing that is necessary for identifying the image regions takes a long time, with the result that for repeat performance of the method steps of recording the second image, determining the first transformation and identifying the image regions, the presentation rate of the second image is too low to perform manipulations on the membrane on the basis of the presented images.

For this reason, the image regions that contain the membrane substantially completely and exclusively are identified only once based on the transformed first image and the recorded second image. Subsequently, a third image is recorded, a second transformation between the second image and the third image is determined such that structures of the retina of the eye are located at mutually corresponding places in the third image and in the second image that has been transformed with the second transformation. Next, a superposition of the third image and the identified image regions which have been transformed with the second transformation is presented.

The steps of recording the third image, determining the second transformation, and presenting the superposition can be performed repeatedly. This repeated performance of method steps does not contain the complicated step of automated image processing for identifying the image regions, which is why a repetition rate of presentations is increased. The second transformation is applied to compensate for displacements of the eye relative to the camera, which occur between the recording of the second image and the recording of the third image, which is why the highlighted presentation of the previously identified image regions in the third image takes place at those places and within that range where the membrane on the retina is contained in the third image.

However, the presentation of the identified image regions which is superposed on the third image is here static, that is, any changes in the shape of the membrane, as can occur for example by partial removal of the membrane, will not be visible in the superposed presentation. It is therefore possible at specific time intervals, for example every 10 seconds, to interrupt the repeated performance of the recording of the third image, of the determining of the second transformation and of the presenting of the superposition, and to rerecord a current second image and to identify, based thereon, those image regions that are then used repeatedly so as to be used in a repetition of the steps of recording the third image, determining the second transformation and presenting the superposition.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
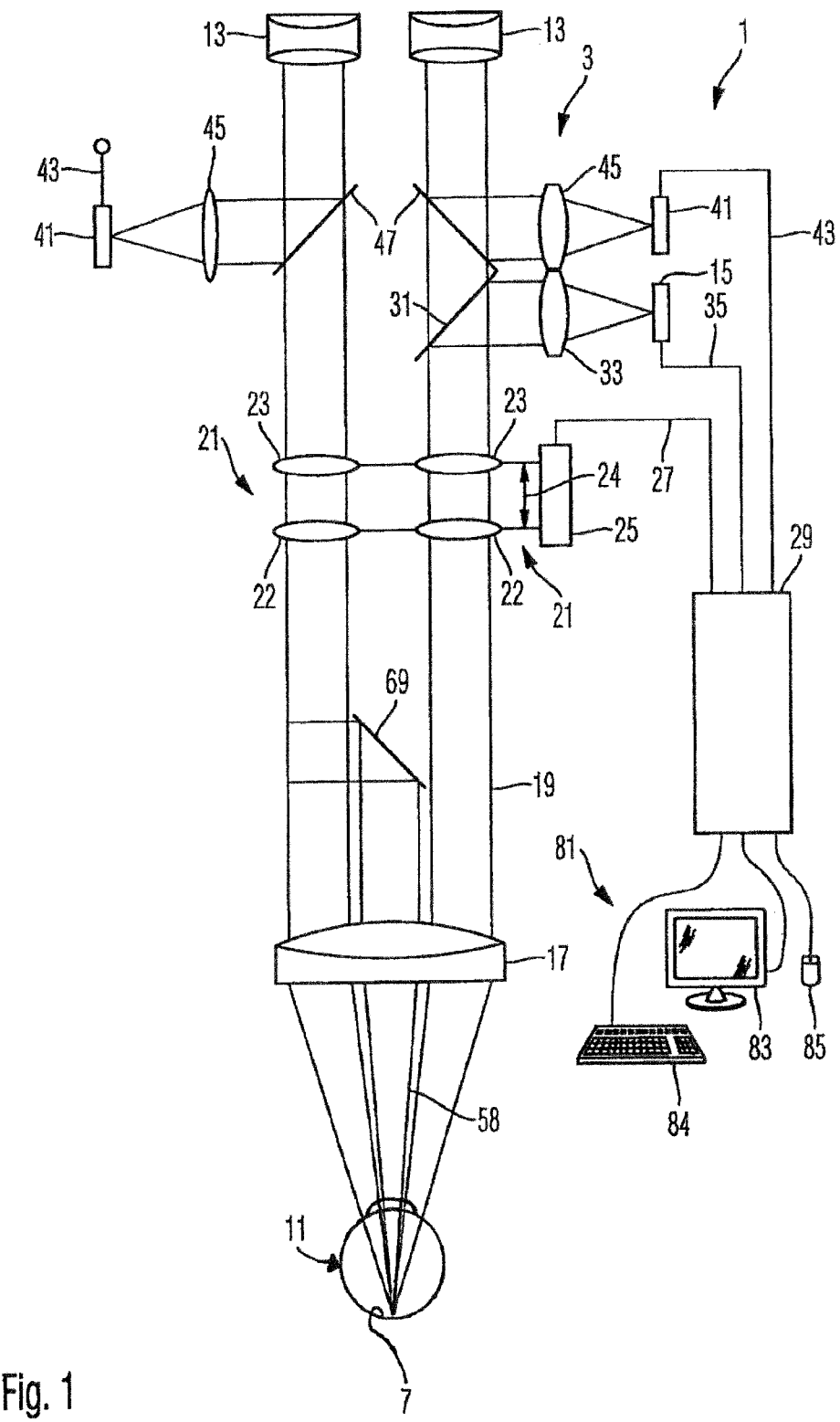
FIG. 1 shows a schematic illustration of one embodiment of a surgical microscope.

FIG. 1 is a schematic of a surgical microscope 1. The surgical microscope 1 includes an imaging optics 3, which is configured to produce images of a retina 7 of an eye 11. Imaging of the retina 7 is carried out using the imaging optics 3 of the illustrated embodiment by a pair of eyepieces 13, into which a surgeon can look with both eyes, and also a camera 15, which can record images of the retina 7 and produce data representing the images.

To this end, the optics 3 has an objective lens 17, which can include one or more lens elements and images, in the example illustrated here, in particular the image field to infinity. Two partial beams 19 are guided in the beam path downstream of the objective lens 17 in each case through a zoom lens arrangement 21, which can change a magnification of the optics. To this end, the two zoom lens arrangements 21 each have at least two lens groups 22 and 23, which are displaceable relative to one another in the beam direction of the partial beams 19, as is indicated in FIG. 1 by way of an arrow 24. The displacement of the two lens groups 22 and 23 relative to one another is steered by an actuator 25, which in turn is controlled by a controller 29 via a control line 27 for setting the magnification of the optics 3.

After the partial beams 19 have passed through the zoom lens arrangement 21, they enter the eyepieces 13, but, from the partial beam 19 shown in FIG. 1 on the right, part of the light of the partial beam 19 is deflected via a partially transmissive mirror 31 and directed onto the camera via a camera adapter optics 33, such that the camera can detect the image of the retina 7. The data produced by the camera 15 is transmitted to the controller 29 via a data link 35.

The optics 3 furthermore includes a display apparatus having two electronic image displays 41, which are fed image data by the controller 29 via a data link 43. The images presented by the image displays 41 are each projected via a projection optics 45 and a partially transmissive mirror 47, which is located in the partial beam 19, into the beam paths to the eyepieces 13, with the result that a user who is looking into the eyepieces 13 can perceive the images which are presented by the displays 41 in superposition with the image of the image field 7 of the object region 11.

Figure 2:
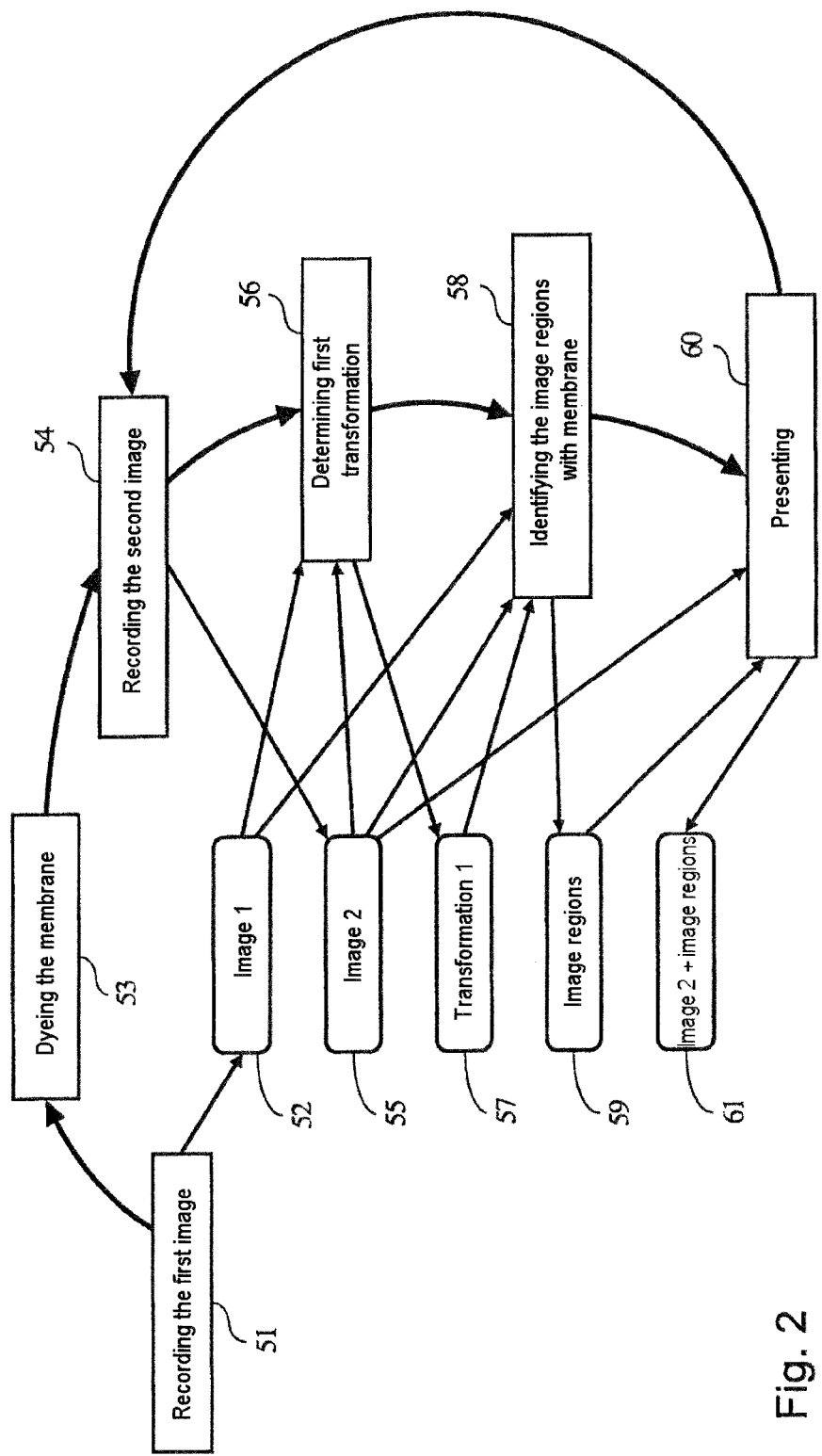
FIG. 2 shows a flowchart of a method for visualizing a membrane on a retina of an eye according to a first embodiment; and, FIG. 3 shows a flowchart of a method for visualizing a membrane on a retina of an eye according to a second embodiment.

FIG. 2 shows a flowchart of a method for visualizing a membrane on the retina 7 of the eye 11. The method starts with recording a first image in a step 51. Recording the first image can be performed with the camera 15 under control by the controller 29 and can be triggered by an action of the user, for example by his operating a switch, such as for example a button of a mouse 85, which is connected to the controller 29, or a key of a keypad 84, which is connected to the controller 29, or by issuing a voice command, which is captured by the controller 29. The first image is stored in the form of image data 52 by the controller 29 in a memory that is assigned to the controller.

In a step 53, the membrane on the retina 7 of the eye 11 is stained with a suitable dye, for example indocyanine green (ICG). Next, a second image is recorded in a step 54, which is stored in the form of image data 55. Recording the second image is triggered and controlled by the controller similarly to the recording of the first image.

Subsequently, in a step 56, an analysis of the first image 52 and of the second image 55 is performed by the controller to determine a first transformation such that mutually corresponding structures of the retina of the eye are located at mutually corresponding places in the second image 55 and in the first image 52 that has been transformed with the first transformation. Parameters that represent this transformation, such as for example image displacement, image rotation and image scaling, are stored in the form of parameter data 57.

Subsequently, in a step 58, image regions which contain the membrane on the retina substantially completely and exclusively are identified in the second image. The identified image regions are stored in the form of data 59.

Subsequently, in a step 60, a presentation is produced which represents the second image and in which the identified image regions 59 are presented in highlighted fashion. Image data 61, which represent this presentation, are produced and presented on a display apparatus of the surgical microscope. The display apparatus can be, for example, a monitor 83 which is connected to the controller 29. However, the presentation can also be produced by the identified image regions being presented on the display apparatus 41 and being superimposed in the beam path to the eyepiece by the partially transmissive mirror 47. The superposition on the direct optical image of the retina 7 takes place here, which is produced by the objective lens 17 and the zoom system 21 and corresponds to the second image 55 which has been recorded by the camera 15, at least as long as no significant displacement of the retina 7 relative to the camera 15 occurs.

The method can be terminated after the complete presentation in step 60 or continue with step 54 in order to repeat it and steps 56, 58 and 60.

Figure 3:
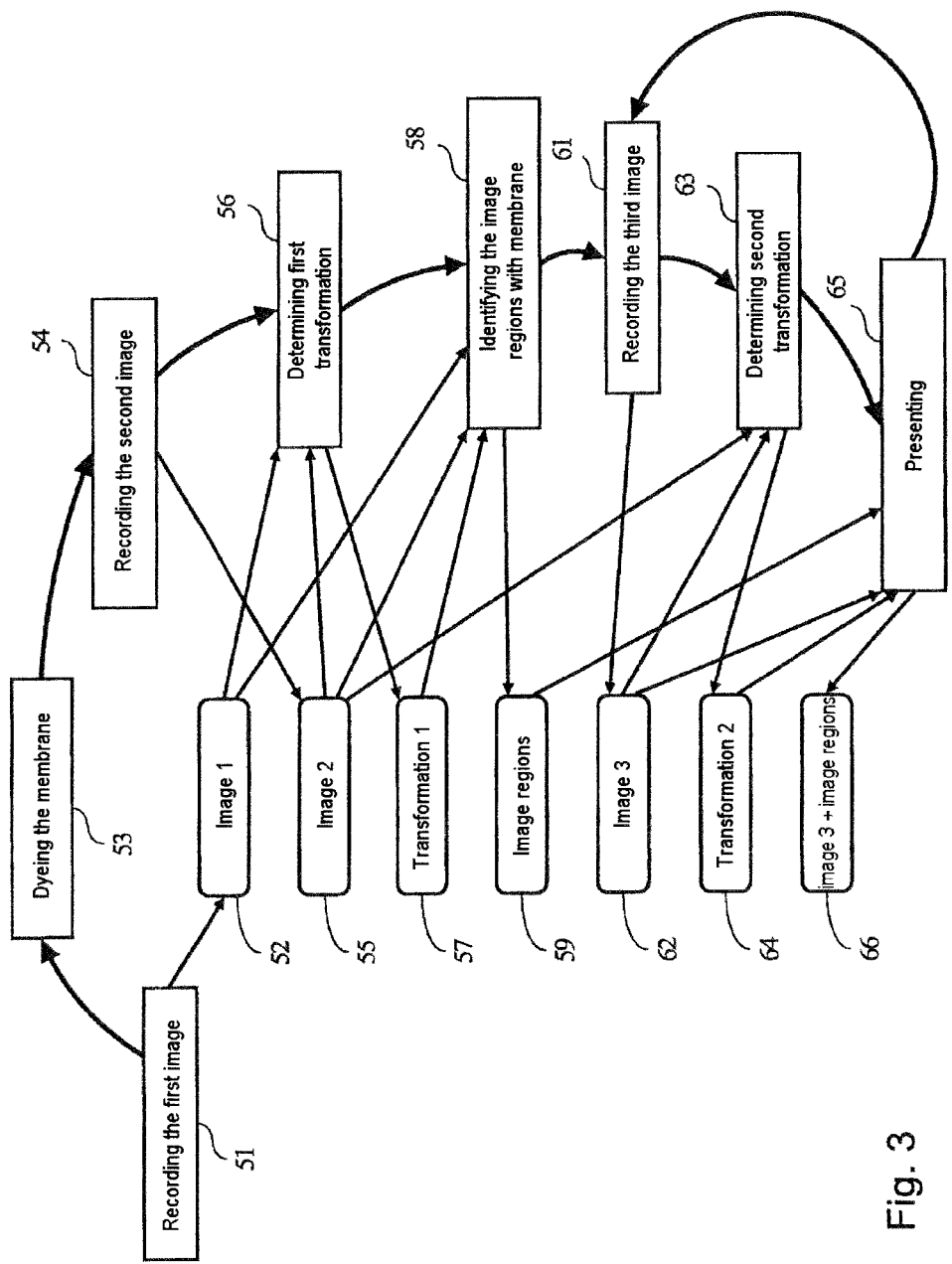

FIG. 3 shows a flowchart of a further embodiment of a method for visualizing a membrane on a retina of an eye. The method in FIG. 3 likewise performs steps 51, 53, 54, 56 and 58 of the method of FIG. 2 in order to produce the image data 52 of the first image, the image data 55 of the second image, the data 57 of the first transformation, and the data 59 of the identified image regions. To this extent, reference is made to the description of the method of FIG. 2. The method of FIG. 3 differs from the method of FIG. 2 in that the presentation of the second image with the highlighted identified image regions (step 60 in FIG. 2) is not produced, but a third image is recorded in a step 61 after the image regions 59 have been identified in step 58. Image data 62 representing this third image are stored.

Subsequently, a second transformation is determined in a step 63 such that mutually corresponding structures of the retina of the eye are located at mutually corresponding places in the third image and in the second image that has been transformed with the second transformation. Data 64 representing parameters of this transformation are stored.

Next, in a step 65, a presentation of the third image in superposition with the identified image regions which have been transformed with the second transformation is produced. Image data 66 representing this presentation can be stored and presented as was explained previously in connection with step 60 of FIG. 2.

After step 65, the method can be terminated or continued at step 61 in order to repeat steps 61, 63 and 65. After a few repetitions of steps 61, 63 and 65, the method can be continued at step 54 in order to record a new, more current second image and to subsequently perform steps 56, 58, 61, 63 and 65.

It is understood that the foregoing description is that of the preferred embodiments of the invention and that various changes and modifications may be made thereto without departing from the spirit and scope of the invention as defined in the appended claims.

What is claimed is:

1. A method for visualizing a membrane on a retina of an eye, the method comprising:
    recording a first image of the retina of the eye with a camera, wherein the membrane on the retina of the eye is not stained;
    applying a dye to the membrane so as to stain the membrane after said recording of said first image;
    recording a second image of the retina of the eye with the camera after the membrane on the retina of the eye has been stained;
    determining a first transformation such that mutually corresponding structures of the retina of the eye are disposed at mutually corresponding places in the second image and in the first image that has been transformed with the first transformation;
    identifying image regions in the second image, which essentially completely contain the membrane on the retina and substantially exclusively contain the membrane on the retina, specifically based on the transformed first image and the recorded second image, wherein the membrane on the retina of the eye is located on a side of the retina facing a posterior vitreous of the eye; and,
    displaying the second image so as to cause the identified image regions in the second image to be highlighted relative to surroundings of the identified image regions.

2. The method of claim 1 further comprising the steps of:
    recording a third image of the retina of the eye after the second image has been recorded;
    determining a second transformation so as to cause mutually corresponding structures of the retina of the eye in the third image and in the second image to be disposed at mutually corresponding locations with the second image having been transformed with the second transformation; and,
    displaying the third image in superposition with the identified image regions which have been transformed with the second transformation.

3. The method of claim 1, wherein said identifying the image regions in the second image includes background removal on at least one of the first and the second image.

4. The method of claim 1, wherein said identifying the image regions in the second image includes background removal on at least one of the first and the second image and digital subtraction between the first and the second image.

5. The method of claim 1, wherein said identifying the image regions in the second image includes digital subtraction between the first and the second image.

6. The method of claim 1 further comprising the step of staining the membrane on the side of the retina facing the posterior vitreous of the eye after the first image has been recorded and before the second image is recorded.

7. The method of claim 2 further comprising the step of staining the membrane on the side of the retina facing the posterior vitreous of the eye after the first image has been recorded and before the second image is recorded.

8. The method of claim 3 further comprising the step of staining the membrane on the side of the retina facing the posterior vitreous of the eye after the first image has been recorded and before the second image is recorded.

9. The method of claim 4 further comprising the step of staining the membrane on the side of the retina facing the posterior vitreous of the eye after the first image has been recorded and before the second image is recorded.

10. The method of claim 5 further comprising the step of staining the membrane on the side of the retina facing the posterior vitreous of the eye after the first image has been recorded and before the second image is recorded.

11. A surgical microscope comprising:
    a microscope optic;
    a camera;
    a display apparatus; and,
    a controller configured to perform a control method which includes:
    recording a first image of a retina of an eye with the camera, wherein a membrane on the retina of the eye is not stained;
    recording a second image of the retina of the eye with the camera after the membrane on the retina of the eye has been stained;
    determining a first transformation such that mutually corresponding structures of the retina of the eye are disposed at mutually corresponding places in the second image and in the first image that has been transformed with the first transformation;
    identifying image regions in the second image, which essentially completely contain the stained membrane on the retina and substantially exclusively contain the stained membrane on the retina, specifically based on the transformed first image and the recorded second image, wherein the membrane on the retina of the eye is located on a side of the retina facing a posterior vitreous of the eye;
    displaying the second image with the display apparatus so as to cause the identified image regions in the second image to be highlighted relative to surroundings of the identified image regions.

12. The surgical microscope of claim 11, wherein said control method further includes:
    recording a third image of the retina of the eye with the camera after the second image has been recorded,
    determining a second transformation so as to cause mutually corresponding structures of the retina of the eye in the third image and in the second image to be disposed at mutually corresponding locations with the second image having been transformed with the second transformation; and,
    displaying the third image with the display apparatus in superposition with the identified image regions which have been transformed with the second transformation.

13. A surgical microscope comprising:
    a microscope optic;

a camera configured to record a first image of a retina of an eye, wherein a membrane on the retina of the eye is not stained;

a display apparatus; and a controller;

said camera being further configured to record a second image of the retina of the eye with the camera after the membrane on the retina of the eye has been stained;

said controller being configured to determine a first transformation so as to cause mutually corresponding structures of the retina of the eye to be disposed at mutually corresponding places in said second image and in said first image that has been transformed with said first transformation;

said controller being further configured to identify image regions in said second image, which essentially completely contain the stained membrane on the retina and essentially exclusively contain the stained membrane on the retina, specifically based on said transformed first image and said recorded second image, wherein the membrane on the retina of the eye is located on a side of the retina facing a posterior vitreous of the eye; and, said display apparatus being configured to display said second image so as to cause the identified image regions in the second image to be highlighted relative to the surroundings of the identified image regions.

14. The surgical microscope of claim 11, wherein:

said camera is further configured to record a third image of the retina of the eye after said second image has been recorded;

said controller is further configured to determine a second transformation so as to cause mutually corresponding structures of the retina of the eye in the third image and in the second image to be disposed at mutually corresponding locations with the second image having been transformed with the second transformation; and, said display apparatus is further configured to display said third image in superposition with the identified image regions which have been transformed with the second transformation.

15. The method of claim 1, wherein the membrane is an epiretinal membrane.

16. The method of claim 1, wherein the membrane is an internal limiting membrane.

* * * * *